(12) United States Patent
Ellis et al.

(10) Patent No.: US 10,016,441 B2
(45) Date of Patent: Jul. 10, 2018

(54) PROSTAGLANDIN CONJUGATES AND DERIVATIVES FOR TREATING GLAUCOMA AND OCULAR HYPERTENSION

(71) Applicant: Novartis AG, Basel (CH)

(72) Inventors: David Archer Ellis, Forth Worth, TX (US); Lukas Scheibler, Telluride, CO (US); Najam A. Sharif, Arlington, TX (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/448,805

(22) Filed: Mar. 3, 2017

(65) Prior Publication Data

US 2017/0239268 A1    Aug. 24, 2017

Related U.S. Application Data

(62) Division of application No. 14/884,074, filed on Oct. 15, 2015, now Pat. No. 9,604,949.

(60) Provisional application No. 62/064,193, filed on Oct. 15, 2014.

(51) Int. Cl.
*A61K 31/5575* (2006.01)
*A61K 47/48* (2006.01)

(52) U.S. Cl.
CPC .... *A61K 31/5575* (2013.01); *A61K 47/48061* (2013.01)

(58) Field of Classification Search
CPC ............ A61K 31/5575; A61K 47/48061
See application file for complete search history.

(56) References Cited

U.S. PATENT DOCUMENTS 5,510,383 A * 4/1996 Bishop ............... A61K 9/0048
514/530

FOREIGN PATENT DOCUMENTS

| WO | 90/02124 A1 | 3/1990 |
| WO | 2013037479 A1 | 3/2013 |
| WO | 2013163219 A1 | 10/2013 |

OTHER PUBLICATIONS

"Product monograph—Travatan Z", Alcon Canada Inc., revised Jan. 6, 2016, pp. 1-24.
MacKay et al., "Dose response for travoprost in the glaucomatous beagle", Veterinary Ophthalmology, 2012, vol. 15, Supp. 1, pp. 31-35.
European Medicines Agency, WC500041987, "EPAR Scientific Discussion Travatan (Travoprost) ", EMEA, 2004, pp. 1-38.
Alcon Laboratories, Inc., "Travatan Z-Travoprost solution/drops", DailyMed, last updated Aug. 17, 2011, found online at https://dailymed.nlm.nih.gov/dailymed/drugInfo.cfm?setid=5549684b-1724-45ca-b67b-590c62b7c149.
Anonymous: "EPAR Scientific Discussion Travatan (Travopost)", Jan. 1, 2004, XP05523678, Retrieved from the Internet: URL: http://www.ema.europa.eu/docs/en_GB/document_library/EPAR_-_Scientific_Discussion/human/000390WC500041987.pdf[retrieved on Dec. 16, 2015].
Megan E. Cavet et al.: "Nitric Oxide (NO): An Emerging Target for the Treatment of Glaucoma", Investigate Opthamology & Visual Science, vol. 55, No. 8, Aug. 14, 2014 (Aug. 14, 2014), p. 5005, XP055465991, US ISSN: 1552-5783, DOI: 10.1167/iovs.14-14515.
Jay L. Katz et al.: "Latanoprostene Bunod 0.024% Significantly Reduces and Maintains Mean Diurnal Intra-Ocular Pressure (IOP) Compared to Latanoprost 0.005% in Subjects with Open Angle Glaucoma or Ocular Hypertension", IOVS ARVO Annual Meeting Abstract, vol. 54, Jun. 1, 2013 (Jun. 1, 2013), p. 460, XP055466142.
Nello Mainolfi et al.: "An Effective Prodrug Strategy to Selectively Enhance Ocular Exposure of a Cannabinoid Receptor (CB1/2) Agonist", Journal of Medicinal Chemistry, vol. 56, No. 13, Jul. 11, 2013 (Jul. 11. 2013), pp. 5464-5472.
Sharif N A et al: "AL-34662: A Potent, Selective, and Efficacious Ocular Hypotensive Serotonin-2 Receptor Agonist", Journal of Ocular Pharmacology and Therapeut, Mary Ann Liebert, Inc., New York, NY, US, vol. 23, No. 1, Jan. 1, 2007 (Jan. 1, 2007), pp. 1-13, XP008109787.
E. Hampton Sessions et al: Benzimidazole- and benzoxazole-based inhibitors of Rho kinase, Bioorganic & Medicinal Chemistry Letters, vol. 18, No. 24, Dec. 1, 2008 (Dec. 1, 2008), pp. 6390-6393.
Larry Keefer: "Nitric Oxide (NO)- and Nitroxyl (HNO)-Generating Diazeniumdiolates (NONOates): Emerging Commercial Opportunities", Current Topics in Medicinal Chemistry, vol. 5, No. 7, Jul. 1, 2005 (Jul. 1, 2005), pp. 325-636.

* cited by examiner

*Primary Examiner* — Pancham Bakshi
(74) *Attorney, Agent, or Firm* — Asha K. Nadipuram

(57) ABSTRACT

Prostaglandin conjugates and derivatives and methods for their use to treat glaucoma and/or lower intraocular pressure are disclosed. Additionally, ophthalmic pharmaceutical compositions useful in the treatment of eye diseases such as glaucoma and elevated intraocular pressure are disclosed. Such compositions comprise an effective amount of prostaglandin conjugates or derivatives of the present invention.

4 Claims, No Drawings

PROSTAGLANDIN CONJUGATES AND DERIVATIVES FOR TREATING GLAUCOMA AND OCULAR HYPERTENSION

TECHNICAL FIELD OF THE INVENTION

The present invention is directed to prostaglandin conjugates and derivatives and their use to treat glaucoma and elevated intraocular pressure. The invention is particularly directed to travoprost conjugates and derivatives and their use for lowering and/or controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated, but no apparent loss of visual function has occurred; such patients are considered to be at high risk for the eventual development of the visual loss associated with glaucoma. Some patients with glaucomatous field loss have relatively low intraocular pressure. These normotension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated.

Drug therapies that have proven to be effective for the reduction of intraocular pressure include both agents that decrease aqueous humor production and agents that increase the outflow facility, uveoscleral and/or conventional outflow. Such therapies are in general administered by one of two possible routes, topically (direct application to the eye) or orally. However, pharmaceutical ocular anti-hypertension approaches have exhibited various undesirable side effects. For example, miotics such as pilocarpine can cause blurring of vision, headaches, and other negative visual side effects. Systemically administered carbonic anhydrase inhibitors can also cause nausea, dyspepsia, fatigue, and metabolic acidosis. Certain prostaglandins cause hyperemia, ocular itching, and darkening of eyelashes and periorbital skin. Further, certain beta-blockers have increasingly become associated with serious pulmonary side-effects attributable to their effects on beta-2 receptors in pulmonary tissue. Sympathomimetics cause tachycardia, arrhythmia and hypertension. Such negative side-effects may lead to decreased patient compliance or to termination of therapy such that normal vision continues to deteriorate. Additionally, there are individuals who simply do not respond well when treated with certain existing glaucoma therapies. There is, therefore, an unmet medical need for other therapeutic agents that lower and control IOP.

SUMMARY OF THE INVENTION

The present invention is directed to the prostaglandin conjugates and derivatives described herein and their use to treat glaucoma and/or lower intraocular pressure. The subject compounds of Formula (I), described below, can be used to lower and/or control IOP associated with normal-tension glaucoma, ocular hypertension, and/or glaucoma in warm blooded animals, including man. In certain embodiments, when used to treat normal-tension glaucoma or ocular hypertension, the compounds may be formulated in pharmaceutically acceptable compositions suitable to for topical delivery to the eye.

Another embodiment of the present invention contemplates an ophthalmic pharmaceutical composition useful in the treatment of glaucoma and control of intraocular pressure, comprising an effective amount of a compound according to Formula (I) disclosed below.

Another embodiment of the present invention comprises a method of lowering intraocular pressure comprising applying a therapeutically effective amount of an ophthalmic pharmaceutical composition useful in the treatment of glaucoma and control of intraocular pressure to the affected eye of a human or other mammal, where the composition comprises an effective amount of a compound according to Formula (I) disclosed below.

The foregoing brief summary broadly describes the features and technical advantages of certain embodiments of the present invention. Additional features and technical advantages will be described in the detailed description of the invention that follows. Novel features which are believed to be characteristic of the invention will be better understood from the detailed description of the invention when considered in connection with any accompanying figures or tables. However, figures or tables provided herein are intended to help illustrate the invention or assist with developing an understanding of the invention, and are not intended to be definitions of the invention's scope.

DETAILED DESCRIPTION OF THE INVENTION

The compounds disclosed and utilized in embodiments of the present invention have the following formula:

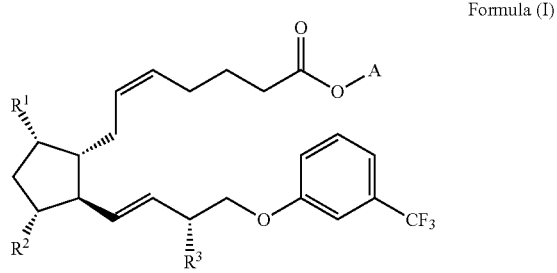

Formula (I)

in which A is selected from the following:

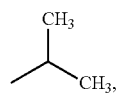

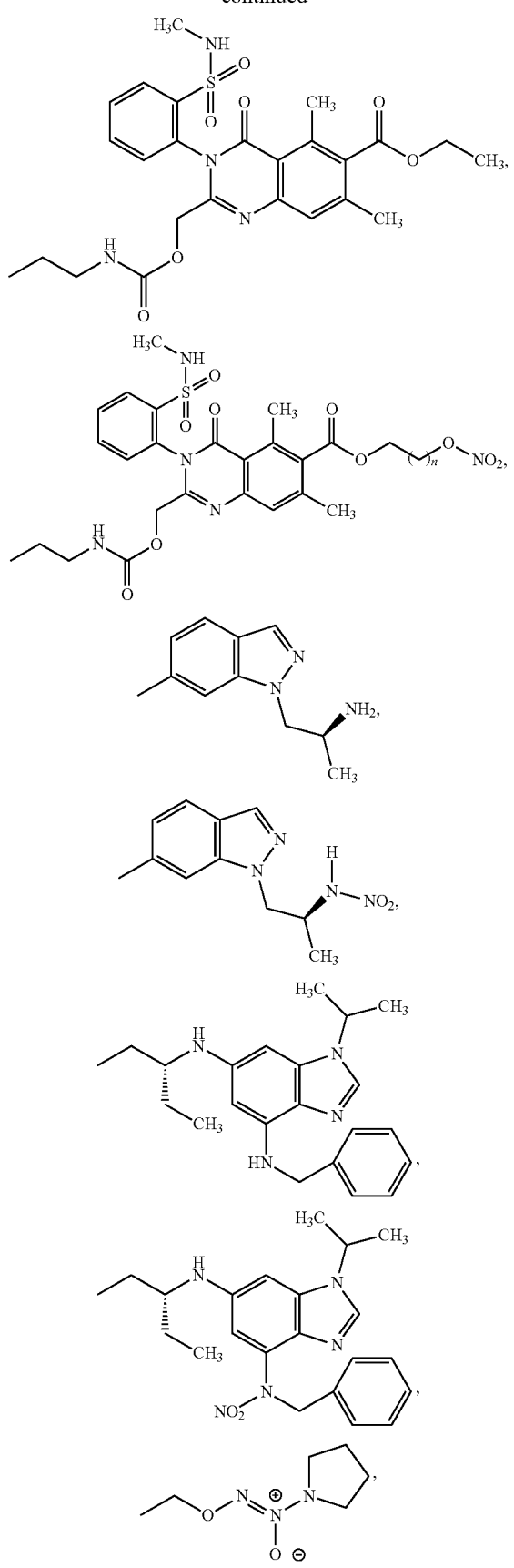
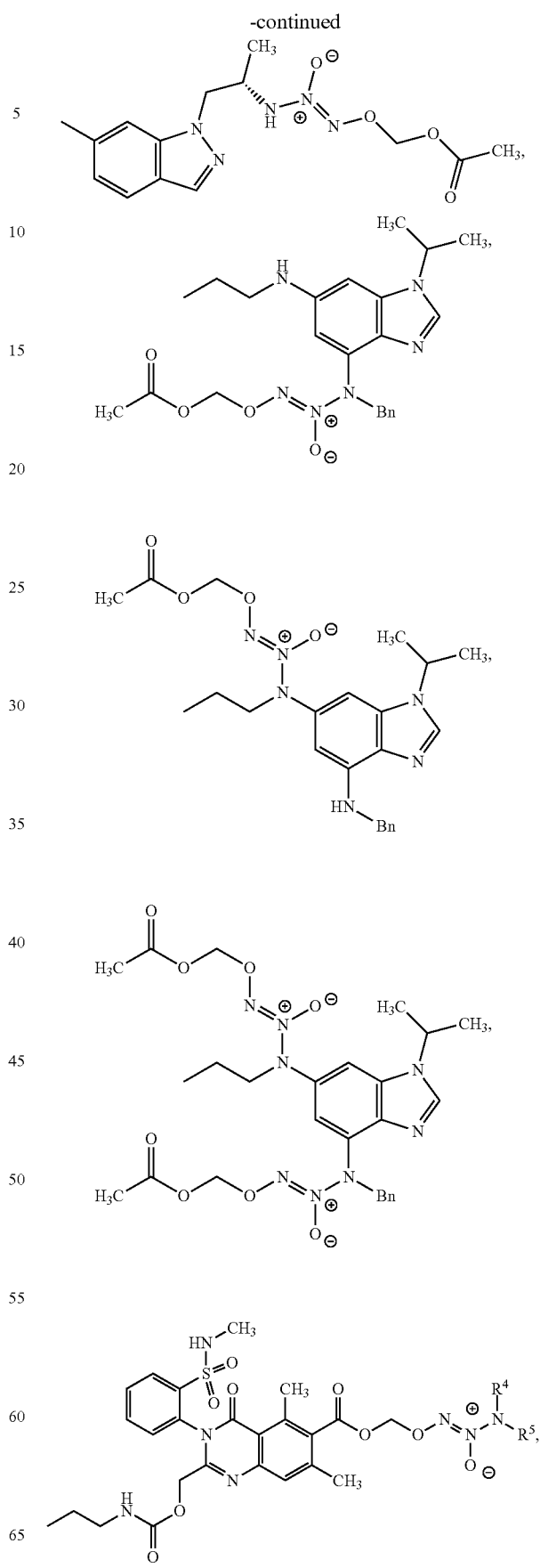

-continued

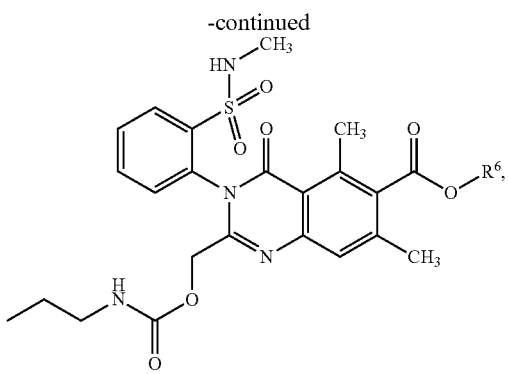

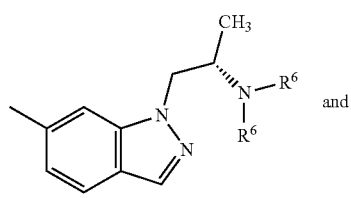
and

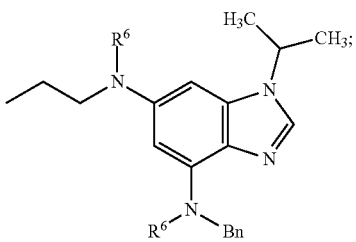

where:
n is 1-6;
R¹, R², R³ independently=OH or O—NO₂;
R⁴, R⁵ independently=H, alkyl, or heteroalkyl; or R⁴ and R⁵ can combine to form cyclic alkyl or cyclic heteroalkyl; and
R⁶ independently=H, NO₂, organic nitrate, organic nitrite, metal—NO complex, sodium nitroprusside (SNP), dinitrosyl iron thiol complex (DNICs), N-nitrosamine, N-hydroxy-N-nitrosamine, N-nitrosimine, nitrosimine, C-nitroso, diazetine dioxide, furoxan, benzofuroxan, oxatriazole-5-imine, sydnonimine, oxime, hydroxylamine, N-hydroxyguanidine, or hydroxyurea.

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

"Aryl", as used herein, represents an aromatic carbocyclic ring system having 6 to 20 carbon atoms, 6 to 15 carbon atoms, or 6 to 10 carbon atoms. It can be monocyclic, bicyclic or tricyclic, and may be optionally substituted as defined. Examples of 6 to 15 carbon aryl groups include but are not limited to phenyl, phenylene, benzenetriyl, indanyl, naphthyl, naphthylene, naphthalenetriyl and anthracenyl.

As used herein, the term "heteroalkyl" refers to a straight- or branched-chain alkyl group preferably having from 2 to 14 carbons, more preferably 2 to 10 carbons, 2 to 7 carbon atoms, or 1 to 4 carbon atoms in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group.

As used herein, the term "cyclic alkyl" refers to saturated or partially unsaturated monocyclic, bicyclic or tricyclic hydrocarbon groups of 3-12 carbon atoms. Unless otherwise provided, cyclic alkyl refers to cyclic hydrocarbon groups having between 3 and 10 ring carbon atoms or between 3 and 7 ring carbon atoms.

As used herein, the term "cyclic heteroalkyl" refers to a 3 to 7 membered monocyclic or 7 to 10 membered saturated or partially saturated ring or ring system, which contains at least one heteroatom selected from N, O and S, where the N and S can also optionally be oxidized to various oxidation states. Cyclic heteroalkyl groups can be attached at a heteroatom or a carbon atom and can include fused or bridged rings.

The term "organic nitrate" means any usual, carbon-containing nitrate. The term refers to polyol esters of nitric acid. Organic nitrates have the general structural formula RONO₂, where R is an aryl or alkyl group. Glyceryl trinitrate (or nitroglycerine) and isosorbide mononitrate are included in this group of organic nitrates as non-limiting examples.

The term "organic nitrite" or "nitrite ester" means any usual, carbon-containing nitrite. Organic nitrites are esters of nitrous acid and contain the nitrosoxy functional group. Organic nitrites have the general structural formula RONO, where R is an aryl or alkyl group.

It is recognized that compounds of Formula (I) can contain one or more chiral centers. This invention contemplates all enantiomers, diastereomers, and mixtures thereof. Furthermore, certain embodiments of the present invention comprise pharmaceutically acceptable salts of compounds according to Formula (I).

Synthesis:

Compounds according to Formula (I) can be synthesized using the general and specific examples set forth below together with information available to those of skill in the art. Publications referred to herein are incorporated by reference in their entirety.

Scheme 1. Synthetic example of O-nitrosylation of prostaglandin conjugates and derivatives.
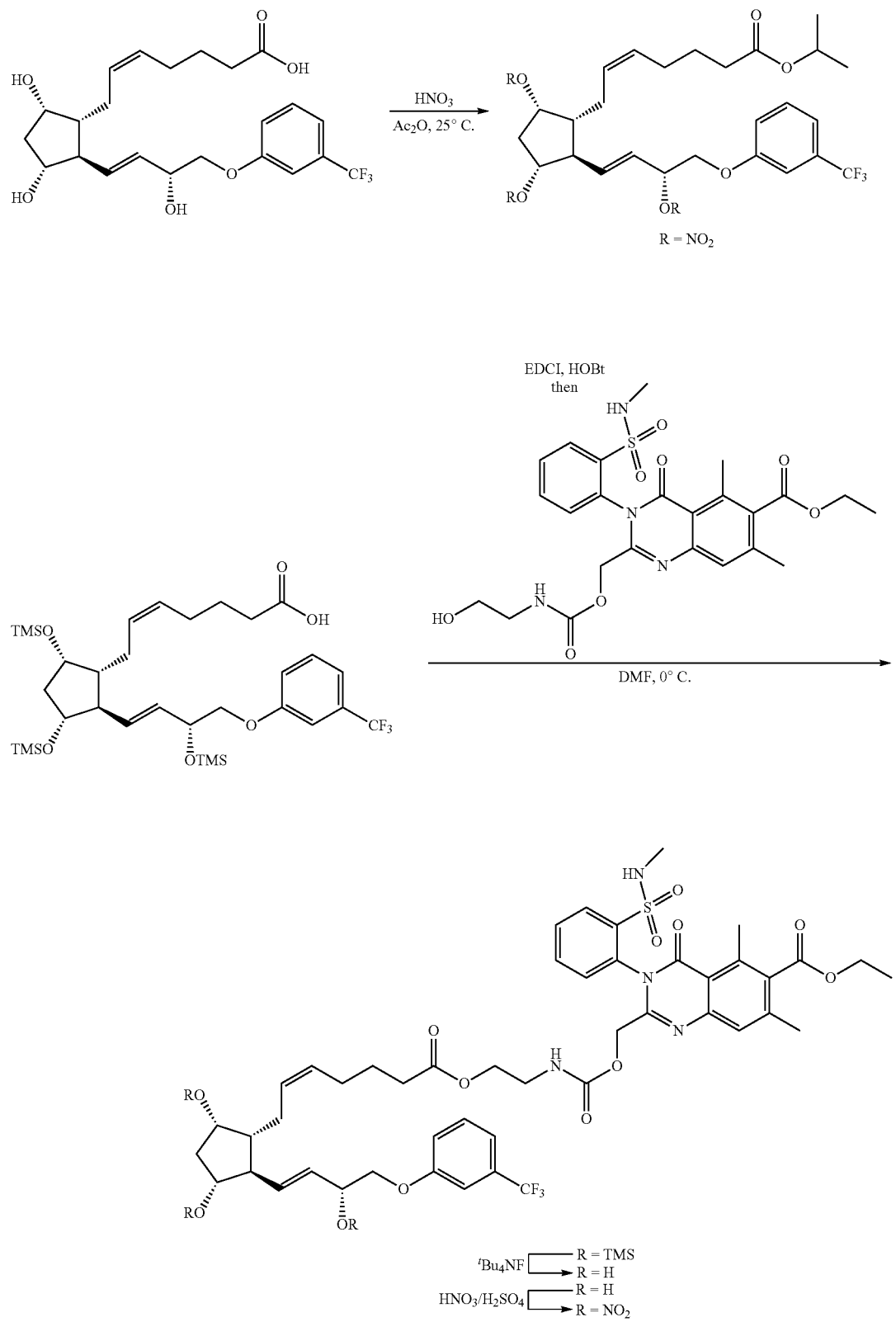

O-NITROSYLATION REFERENCE
Baker, J. W.; et al. *Chem. Ind.* 1954, 465
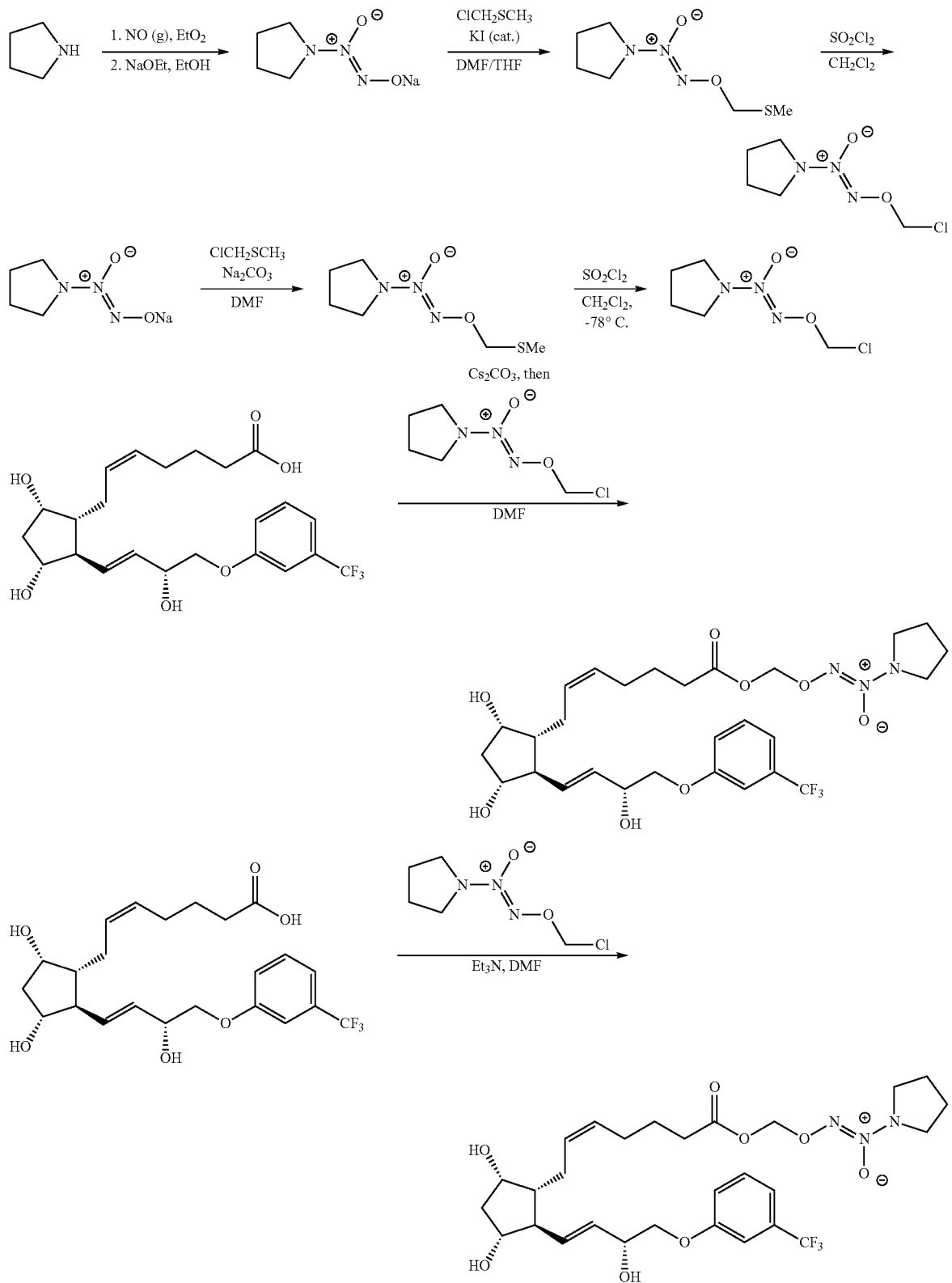
Scheme 2. Synthetic examples of diazeniumdiolate prostaglandin conjugates and derivatives.

-continued
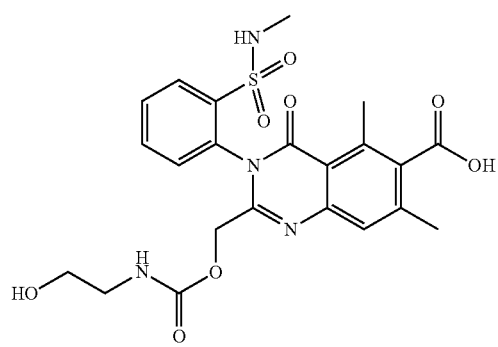 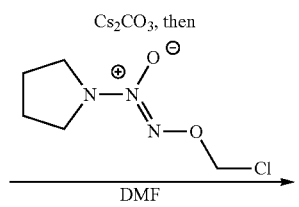
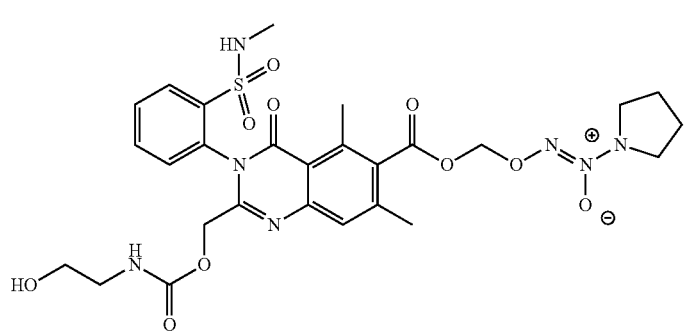 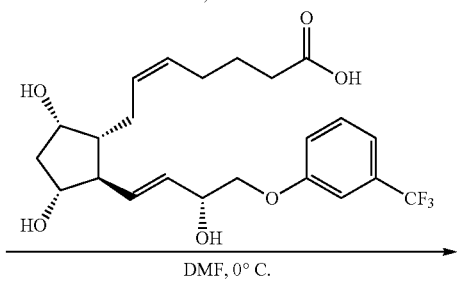
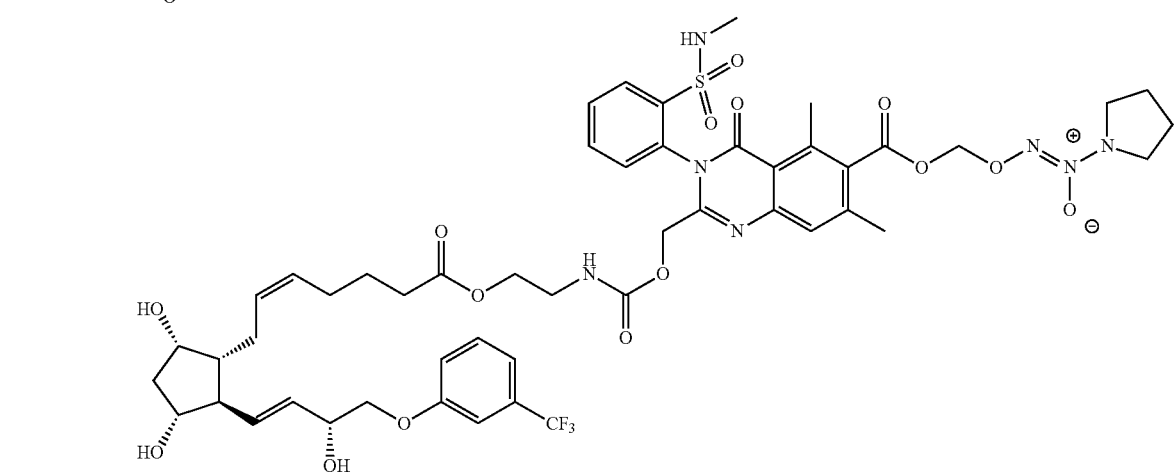
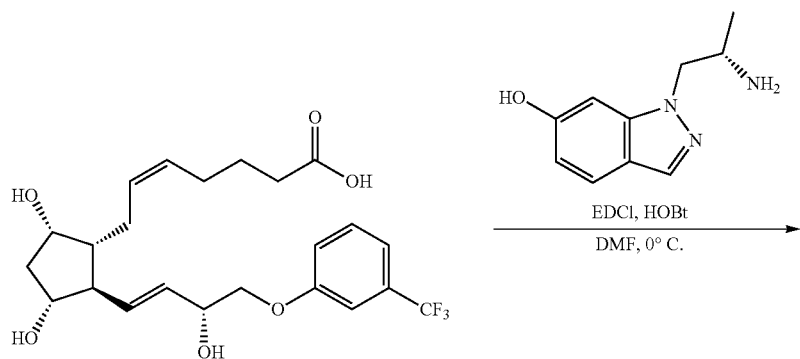

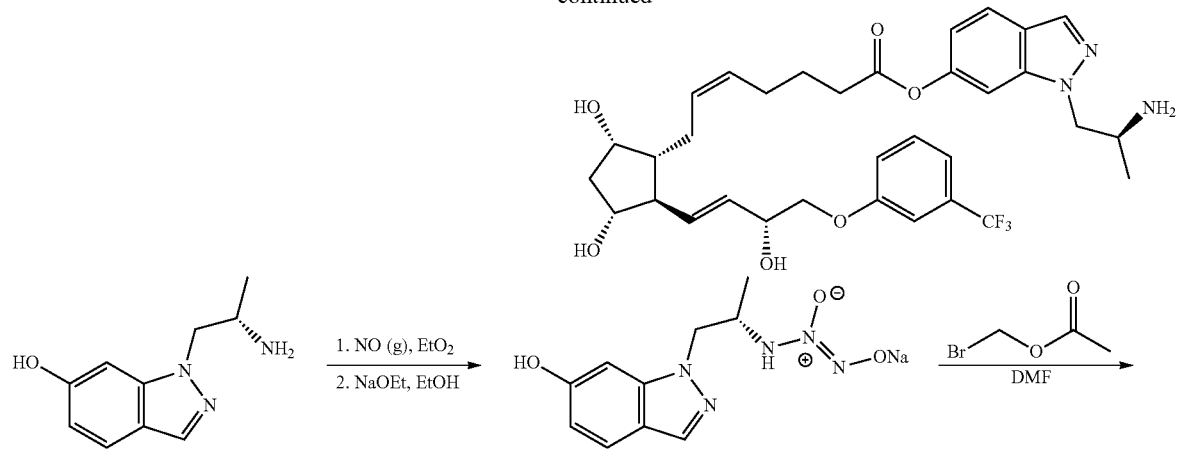

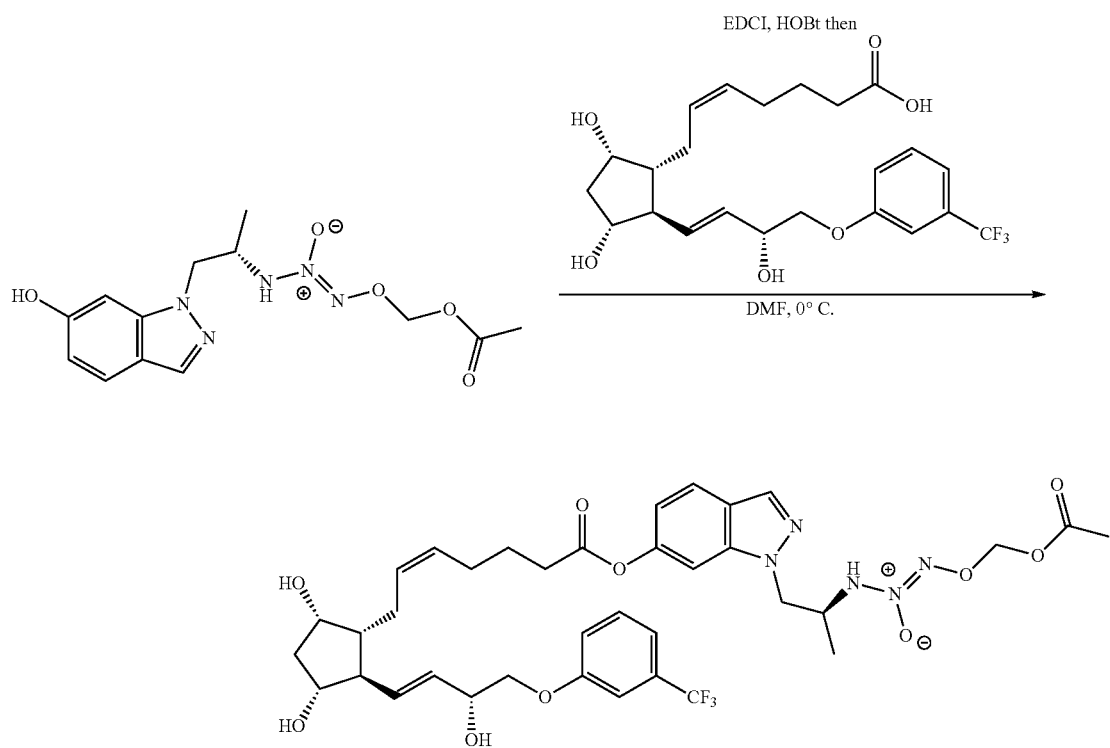

DIAZENIUMDIOLATE REFERENCES

1. Drago, R. S.; et al. *J. Am. Chem. Soc.* 1960, 82, 96-98
2. Drago, R. S.; et al. *J. Am. Chem. Soc.* 1961, 83, 1819-1822
3. Margos, C. M.; et al. *J. Med. Chem.* 1991, 34, 3242-3247
4. Saavedra, J. E.; et al. *J. Med. Chem.* 2000, 43, 261-269
5. Konter, J.; et al. *Bioorg. Med. Chem. Lett.* 2008, 16, 8294-8300
6. Saavedra, J. E.; et al. *J. Org. Chem.* 1992, 57, 6134-6138

The following Examples illustrate synthesis of selected compounds of Formula (I) and provide methods that can be adapted to synthesis of other compounds of Formula (I).

Example 1

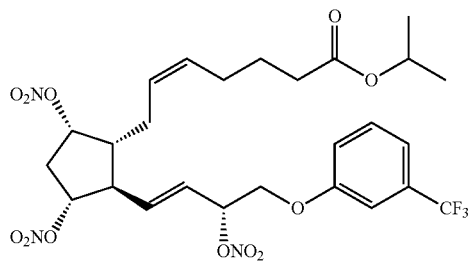

Isopropyl (Z)-7-((1R,2R,3R,5S)-3,5-bis(nitrooxy)-2-((R,E)-3-(nitrooxy)-4-(3-(trifluoromethyl)phenoxy)but-1-en-1-yl)cyclopentyl)hept-5-enoate Travoprost (928 mg, 1.85 mmol) was dissolved in DCM (12 mL) and cooled to 0° C. in an ice-bath. Acetic anhydride (2.3 mL, 5V to nitric acid) was cooled to 0° C. and white fuming nitric acid (699 mg, 472 μL, 6.0 eq, >99% purity) was added carefully to the to acetic anhydride and mixed for 5 min. The nitric acid/acetic anhydride solution was added dropwise to the DCM solution of travoprost over 4 min. The reaction mixture was stirred for 10 min., diluted with DCM (50 mL) and quenched with sodium bicarbonate solution (12 mL water, 12 mL sat. sodium bicarbonate solution). The phases were separated and the organic layer was washed sequentially with saturated aqueous sodium bicarbonate and brine (25 mL), dried over MgSO$_4$, filtered and concentrated under reduced pressure. The crude was chromatographed on silica and gave the title compound as a colorless oil (1.03 g, 88%). $^1$H NMR (400 MHz, CDCl$_3$) δ ppm 7.42 (t, J=8.0 Hz, 1H), 7.28-7.26 (m, 1H), 7.12 (s, 1H), 7.08-7.06 (m, 1H), 5.96-5.90 (m, 1H), 5.79-5.73 (m 2H), 5.48-5.42 (m, 1H), 5.34-5.26 (m, 2H), 5.16 (ddd, J=8.7, 7.0, 3.5 Hz, 1H), 5.03-4.93 (m, 1H), 4.21-4.17 (m, 2H), 2.78-2.66 (m, 2H), 2.27-2.20 (m, 2H), 2.17-1.93 (m, 5H), 1.67-1.58 (m, 2H), 1.21 (dd, J=6.3, 2.8 Hz, 6H); $^{13}$C NMR (100 MHz, CDCl$_3$) δ 173.1, 158.1, 135.7, 132.5 (q, $^2J_{CF}$=32 Hz) 132.1, 130.4, 126.3, 126.1, 124.2 (q, $^1J_{CF}$=271 Hz), 118.6 (q, $^3J_{CF}$=4.0 Hz), 118.2, 111.5 (q, $^3J_{CF}$=4.0 Hz), 85.5, 82.5, 80.5, 67.7, 67.5, 50.8, 47.6, 37.3, 34.0, 26.6, 24.8, 24.6, 22.0; $^{19}$F NMR (376 MHz, CDCl$_3$) δ −62.73; IR (KBr) ν 2981, 1720, 1638, 1450, 1330, 1275, 1127, 855; MS (ES+) m/z 636.20 (M+H)$^+$, 653.29 (M+NH$_4$)$^+$, 658.26 (M+Na)$^+$, 573.35 (M-NO$_3$).

Example 2

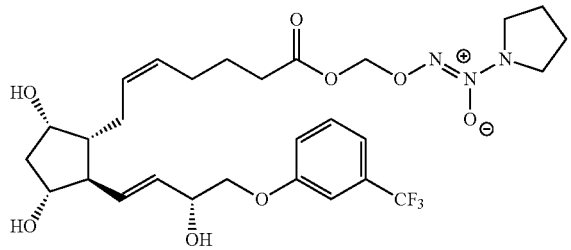 [SMILES: O=C(CCC/C=C\C[C@@H]1[C@@H](/C=C/[C@@H](O)COc2cccc(C(F)(F)F)c2)[C@H](O)C[C@@H]1O)OCO/N=[N+](\[O-])N1CCCC1]

Pyrrolidine NONOate:

To pyrrolidine (55 mL, 46.8 g, 657 mmol) placed in a glass-lined 2 L pressure vessel was added a 25 wt % sodium methoxide solution in methanol (172 mL, 756 mmol, 1.15 eq) followed by MeCN (165 mL, 3V) and MTBE (165 mL, 3V). The headspace was purged with nitrogen and the solution was degassed with nitrogen. The headspace was then purged with NO gas and then pressurized to 3 bar. The reaction mixture was run under agitation. Rapid gas-uptake was observed with an exotherm (28° C.). The pressure was kept at 3 bar and after 4 h no further uptake was observed. The vessel was vented and purged with nitrogen. The resulting white precipitate was filtered and washed with MTBE (20 mL) to provide 72 g (72%) of desired product as a white solid.

(Z)-2-((methylthio)methoxy)-1-(pyrrolidin-1-yl)diazene 1-oxide: To a dried 500 mL RBF under nitrogen atmosphere was added anhydrous sodium carbonate (7.42 g, 70.0 mmol, 0.7 eq), anhydrous DMF (200 mL, 13 V) and chloromethyl methylsulfide (10.0 mL, 120.0 mmol, 1.2 eq). The reaction mixture was stirred for 5 min at ambient temperature. The reaction was treated with NONOate (15.3 g, 100.0 mmol) resulting in a color change from yellow to pink. The reaction mixture was stirred for 16 h at 25° C., diluted with EtOAc (50 mL) and filtered over celite. The filtrate was diluted with water (100 mL) and extracted with MTBE (2×200 mL). The combined organic layers were washed with 10% brine (3×200 mL), dried over MgSO4, filtered and concentrated. The crude material was purified by automated flash chromatography to give the desired product as a pale yellow oil (3.97 g, 21%). 1H NMR (400 MHz, CDCl3) δ ppm 5.18 (s, 2H), 3.55-3.51 (m, 4H), 2.23 (s, 3H), 1.93-1.90 (m, 4H).

(Z)-2-(chloromethoxy)-1-(pyrrolidin-1-yl)diazene 1-oxide

To a 250 mL three-necked flask, equipped with thermoprobe, nitrogen-inlet and addition funnel was added (Z)-2-((methylthio)methoxy)-1-(pyrrolidin-1-yl)diazene 1-oxide (3.97 g, 20.7 mmol). The reaction vessel was charged with DCM (100 mL) and the reaction mixture was cooled to −78° C. followed by dropwise addition of a 1M solution of sulfurylchloride in DCM (3.35 g, 2 ml, 24.8 mmol, 1.2 eq in 25 mL DCM). After complete addition, the reaction mixture was allowed to warm to ambient temperature and stirred for 3 h. The reaction mixture was washed sequentially with water (50 mL), saturated aqueous sodium bicarbonate (50 mL), brine (50 mL). The organics were dried over MgSO$_4$, filtered, and concentrated in vacuo to give a brown oil (3.61 g, 90%). $^1$H NMR (400 MHz, CDCl$_3$) δ ppm 5.83 (s, 2H), 3.64-3.62 (m, 4H), 1.99-1.96 (m, 4H); $^{13}$C NMR (100 MHz, CDCl$_3$) δ 79.6, 50.6, 23.1; MS (ES+) 180.1 (M+H)$^+$.

(Z)-2-((((Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoyl)oxy)methoxy)-1-(pyrrolidin-1-yl)diazene 1-oxide Travoprost acid (3.4 g, 7.41 mmol) in MeCN (22 mL) was treated sequentially with trimethylamine and a solution of (Z)-2-(chloromethoxy)-1-(pyrrolidin-1-yl)diazene 1-oxide (1.6 g, 8.9 mmol, 1.2 eq) in MeCN (8 mL). The resulting solution was stirred at 25° C. for 16 h. The solvent was removed under reduced pressure. The resulting residue was taken up in water (35 mL), extracted with EtOAc (2×50 mL). The combined organics were washed with brine (25 mL), dried over MgSO$_4$, filtered and concentrated under reduced pressure. The crude material was purified by column chromatography to give the desired product as a pale yellow oil (1.42 g, 40%). $^1$H NMR (400 MHz, CDCl$_3$) δ ppm 7.41-7.37 (m, 1H), 7.22-7.20 (m, 1H), 7.15 (s, 1H), 7.10-7.08 (m, 1H), 5.77-5.64 (m, 4H), 5.46-5.27 (m, 2H), 4.54 (m, 1H), 4.18-4.17 (m 1H), 4.03-3.93 (m, 3H), 3.58-3.55 (m, 4H), 2.69-2.68 (m, 1H, exchangeable hydroxyl groups), 2.62-2.60 (m, 1H, exchangeable hydroxyl groups), 2.41-2.04 (m, 9H), 1.98-1.91 (m, 4H), 1.79-1.76 (m, 1H), 1.72-1.64 (m 2H), 1.58-1.51 (m, 1H); $^{13}$C NMR (100 MHz, CDCl$_3$) δ 172.5, 158.7, 135.3, 131.9 (q, $^2J_{CF}$=32.4 Hz), 130.1, 129.5, 129.5, 129.3, 123.9 (q, $^1J_{CF}$=272.3 Hz), 118.1, 117.8 (q, $^3J_{CF}$=3.8 Hz), 111.5 (q, $^3J_{CF}$=3.9 Hz), 87.3, 78.0, 73.0, 72.1, 70.8, 56.0, 50.7, 50.4, 42.9, 33.3, 26.4, 25.7, 24.4, 23.0; $^{19}$F NMR (376 MHz, CDCl$_3$) δ −62.67; MS (ES−) m/z 646 (M+45)$^-$ [M+formate].

Modes of Delivery:

The compounds of Formula (I) can be incorporated into various types of ophthalmic formulations for delivery. The Formula (I) compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, to dermal or nasal delivery) using techniques well known by those of ordinary skill in the art. It is further contemplated that the agents of the invention may be formulated in intraocular insert or implant devices.

The compounds of Formula (I) are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

The compounds of Formula (I) are preferably formulated as topical ophthalmic suspensions or solutions, with a pH of about 4 to 8. The compounds are contained in the composition in amounts sufficient to lower IOP in patients experiencing elevated IOP and/or maintaining normal IOP levels in glaucoma patients. Such amounts are referred to herein as "an amount effective to control IOP," or more simply "an effective amount." The compounds will normally be contained in these formulations in an amount 0.0001 to 5 percent by weight/volume ("w/v %"), but preferably in an amount of 0.001 to 2 w/v % and most preferred in an amount of 0.01 to 1.0 w/v %. Thus, for topical presentation 1 to 2 drops of these formulations would be delivered to the surface of the eye 1 to 4 times per day, according to the discretion of a skilled clinician.

The compounds of Formula (I) can also be used in combination with other glaucoma treatment agents, such as, but not limited to, β-blockers, prostaglandin analogs, carbonic anhydrase inhibitors, $\alpha_2$ agonists, rho kinase inhibitors, miotics, and neuroprotectants.

The following examples are provided to illustrate certain embodiments of the invention, but should not be construed as implying any limitations to the claims. The phrase "Compound of Formula (I)" in Examples 1-4 means that the formulation described in the respective Example is believed to be suitable for any compound according to Formula (I).

Composition Example 1

| Ingredients | Concentration (w/v %) |
|---|---|
| Compound of Formula (I) | 0.001-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Composition Example 2

| Ingredients | Concentration (w/v %) |
|---|---|
| Compound of Formula (I) | 0.001-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Composition Example 3

| Ingredients | Concentration (w/v %) |
|---|---|
| Compound of Formula (I) | 0.001-2% |
| Guar gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Composition Example 4

| Ingredients | Concentration (w/v %) |
|---|---|
| Compound of Formula (I) | 0.001-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

What is claimed is:

1. A compound represented by Formula (I):

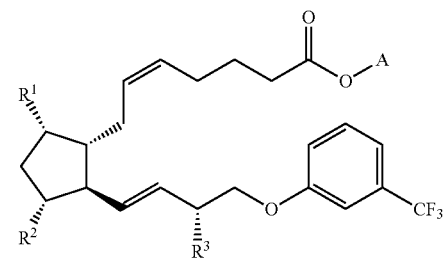

Formula (I)

in which A is selected from the group consisting of:

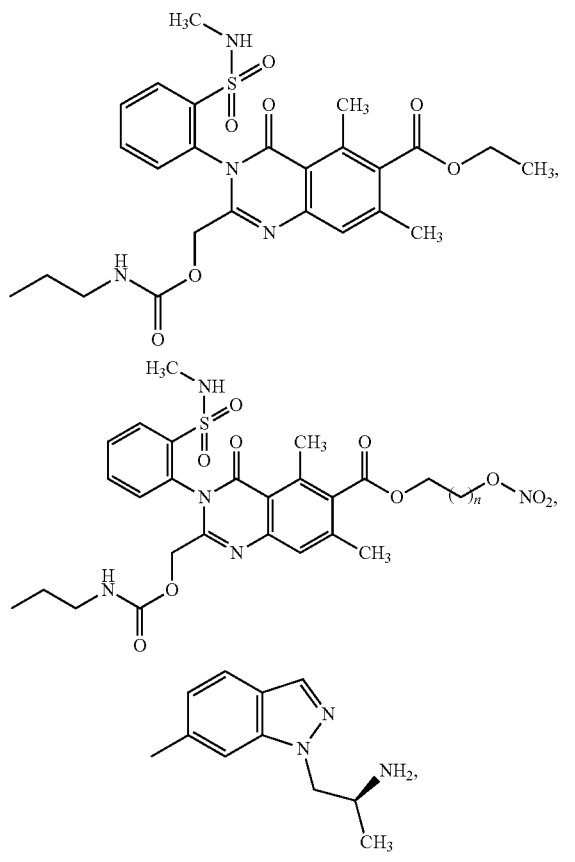

-continued

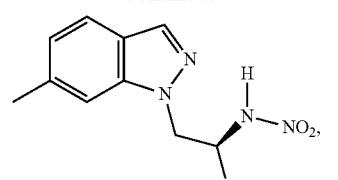

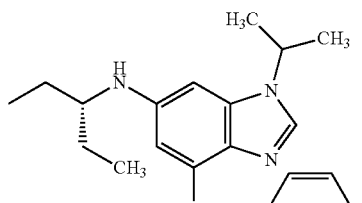

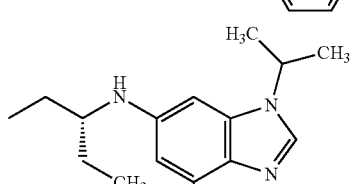

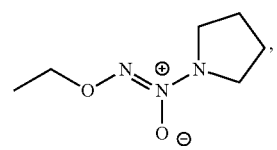

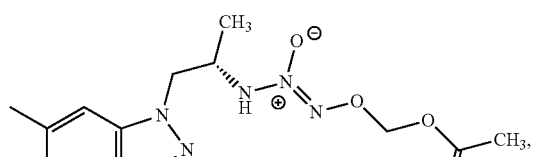

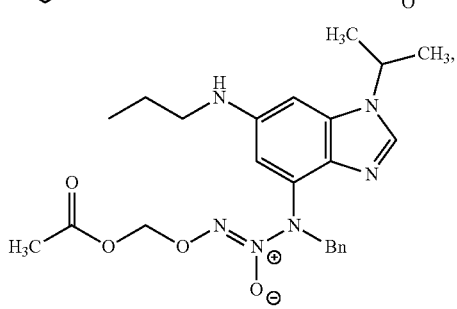

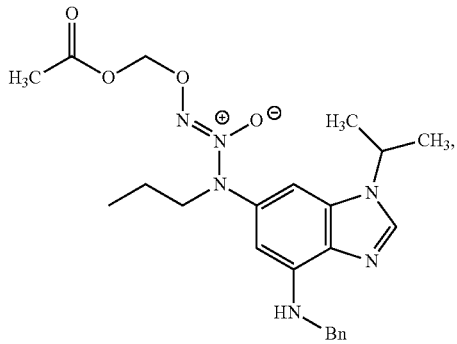

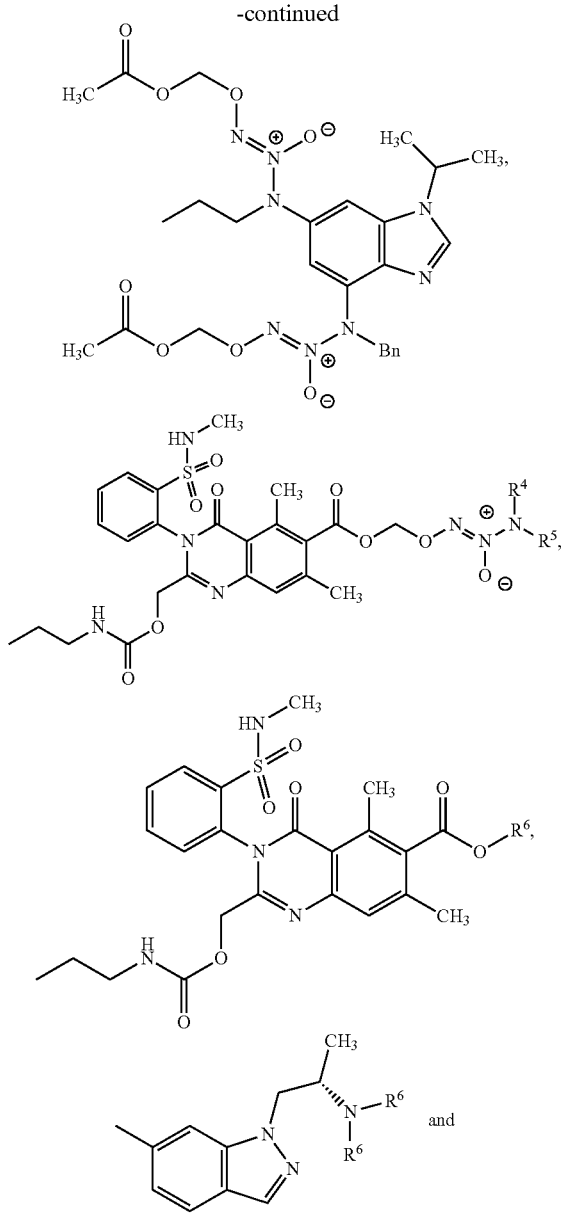

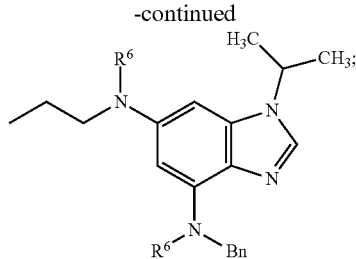

where:

n is 1-6;

R$^1$, R$^2$, R$^3$ independently=OH or O—NO$_2$;

R$^4$, R$^5$ independently=H, alkyl, or heteroalkyl; or R$^4$ and R$^5$ can combine to form cyclic alkyl or cyclic heteroalkyl; and R$^6$ independently=H, NO$_2$, organic nitrate, organic nitrite, metal—NO complex, sodium nitroprusside (SNP), dinitrosyl iron thiol complex (DNICs), N-nitrosamine, N-hydroxy-N-nitrosamine, N-nitrosimine, nitrosimine, C-nitroso, diazetine dioxide, furoxan, benzofuroxan, oxatriazole-5-imine, sydnonimine, oxime, hydroxylamine, N-hydroxyguanidine, or hydroxyurea.

2. The compound of claim 1 wherein the compound is a pharmaceutically acceptable salt of a compound according to Formula (I).

3. A compound selected from the group consisting of: Isopropyl (Z)-7-((1R,2R,3R,5S)-3,5-bis(nitrooxy)-2-((R,E)-3-(nitrooxy)-4-(3-(trifluoromethyl)phenoxy)but-1-en-1-yl)cyclopentyl)hept-5-enoate and (Z)-2-((((Z)-7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoyl)oxy)methoxy)-1-(pyrrolidin-1-yl)diazene 1-oxide.

4. The compound of claim 3, wherein the compound is a pharmaceutically acceptable salt.

* * * * *